US006952950B2

(12) United States Patent
Doe et al.

(10) Patent No.: US 6,952,950 B2
(45) Date of Patent: Oct. 11, 2005

(54) SYSTEM AND METHOD FOR AUTOMATIC IDENTIFICATION OF A DETACHABLE COMPONENT OF AN INSTRUMENT

(75) Inventors: Nigel Doe, West Sussex (GB); Peter Foster, Surrey (GB)

(73) Assignee: Waters Investment Limited, New Castle, DE (US)

( * ) Notice: Subject to any disclaimer, the term of this patent is extended or adjusted under 35 U.S.C. 154(b) by 0 days.

(21) Appl. No.: 10/382,589

(22) Filed: Mar. 7, 2003

(65) Prior Publication Data

US 2004/0173009 A1 Sep. 9, 2004

(51) Int. Cl.[7] .......................... G01N 11/14; G01N 11/16
(52) U.S. Cl. ..................... 73/54.01; 73/54.02; 73/865.8
(58) Field of Search ............................ 73/54.01, 54.02, 73/865.8; 235/435–495

(56) References Cited

U.S. PATENT DOCUMENTS

| | | | | |
|---|---|---|---|---|
| 2,679,157 A | * | 5/1954 | Carpenter ................... | 73/54.31 |
| 3,185,949 A | * | 5/1965 | Jordan ......................... | 338/131 |
| 3,251,150 A | * | 5/1966 | Sedgwick et al. ............ | 40/625 |
| 3,644,715 A | * | 2/1972 | Holderith ..................... | 235/442 |
| 3,816,710 A | * | 6/1974 | Hoffman et al. ............. | 235/444 |
| 3,965,722 A | * | 6/1976 | Bagg et al. ................. | 73/54.31 |
| 4,524,611 A | | 6/1985 | Richon et al. | |
| 4,602,501 A | | 7/1986 | Hirata | |
| 4,643,021 A | * | 2/1987 | Mattout ....................... | 73/54.28 |
| RE32,837 E | * | 1/1989 | Corni .......................... | 235/375 |
| 5,040,410 A | | 8/1991 | Chu et al. | |
| 5,394,739 A | * | 3/1995 | Garvey et al. ............. | 73/54.23 |
| 5,591,403 A | * | 1/1997 | Gavin et al. ................... | 422/73 |
| 5,800,781 A | * | 9/1998 | Gavin et al. ................... | 422/73 |
| 5,962,215 A | * | 10/1999 | Douglas et al. ................ | 435/4 |
| 6,018,988 A | | 2/2000 | Persson | |
| 6,149,060 A | * | 11/2000 | Meadows ............... | 235/462.01 |
| 6,202,496 B1 | * | 3/2001 | Jakob et al. ................... | 73/866 |
| 6,499,336 B1 | | 12/2002 | Raffer | |
| 6,531,095 B2 | * | 3/2003 | Hammer et al. ............... | 422/64 |
| 6,591,664 B2 | * | 7/2003 | Litton ........................ | 73/54.41 |
| 6,663,576 B2 | * | 12/2003 | Gombrich et al. ........... | 600/562 |
| 2002/0031446 A1 | * | 3/2002 | Friedlander et al. ....... | 422/68.1 |
| 2002/0040196 A1 | * | 4/2002 | Kensey et al. .............. | 600/573 |
| 2002/0110494 A1 | * | 8/2002 | Lemme et al. .............. | 422/100 |
| 2002/0111741 A1 | * | 8/2002 | Abraham-Fuchs et al. .... | 702/19 |
| 2002/0137708 A1 | * | 9/2002 | Kluttz et al. ............. | 435/287.2 |
| 2003/0116625 A1 | * | 6/2003 | Litwiller et al. ............ | 235/444 |
| 2003/0136840 A1 | * | 7/2003 | Wu et al. ............... | 235/462.01 |
| 2003/0170143 A1 | * | 9/2003 | Cunningham ................ | 422/57 |
| 2003/0170882 A1 | * | 9/2003 | Smith et al. ............. | 435/287.2 |

FOREIGN PATENT DOCUMENTS

JP          62209683 A    *   9/1987            G06K/7/04

OTHER PUBLICATIONS

Inernational Search Report dated Oct. 12, 2004.
Written Opinion of the International Searching Authority.

\* cited by examiner

*Primary Examiner*—Hezron Williams
*Assistant Examiner*—David A. Rogers
(74) *Attorney, Agent, or Firm*—Pillsbury Winthrop Shaw Pittman LLP

(57) ABSTRACT

A system and method for automatic identification of a detachable component of an instrument is disclosed. The detachable component includes a machine-readable device that contains information associated with the detachable component. The machine-readable device can be a bar code, a variable depth pattern, a magnetic stripe, or the like. The information contained within the machine-readable device can include one or more of serial number, type, material, dimensions, and calibration data of the detachable component. The instrument includes a reader that is configured to obtain the information from the machine-readable device.

21 Claims, 6 Drawing Sheets

KNOWN ART

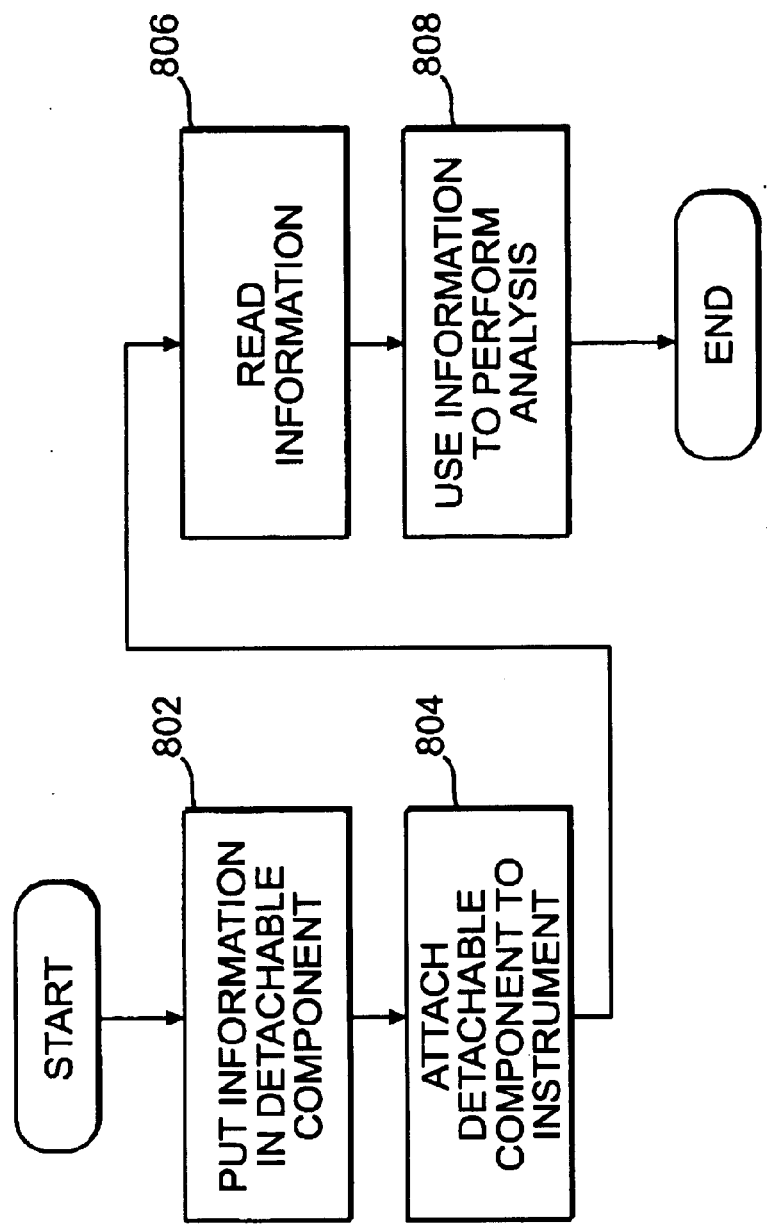

SYSTEM AND METHOD FOR AUTOMATIC IDENTIFICATION OF A DETACHABLE COMPONENT OF AN INSTRUMENT

BACKGROUND

1. Field of the Invention

The present invention relates generally to a material testing instrument and, more particularly, to a system and method for identification of a detachable component of an instrument.

2. Background of the Invention

A rheometer is a device that measures stress and strain associated with a specimen or a test sample during material testing. TA Instruments Ltd, Leatherhead, Surrey, England, which is a subsidiary of TA Instruments, New Castle, Del., manufactures a number of rheometers, including Models AR 550, AR 1000, and AR 2000.

The AR 550 is a general purpose rheometer with many features of a research grade system. The AR 550 is an upgradeable system, which means it can be upgraded as its user's applications expand. A variation of the AR 550 is the QCR II that can be used to transfer Theological tests from a laboratory to a manufacturing facility or a quality control laboratory. The QCR II is a robust rheometer that easily automates the analysis of a broad range of samples.

The AR 1000 is a research grade rheometer incorporating a unique motor design and advanced material air bearing. It has excellent torque performance and very low inertia. The AR 1000 can be equipped with multiple temperature control options, a normal force sensor, and custom geometries.

The AR 2000 is currently the most advanced rheometer. Its innovative Mobius Drive™ offers unprecedented controlled strain and controlled stress performance. The AR 2000's unique features include its broad torque range, superior strain resolution, wide frequency range, and ingenious convenience features, like the Smart Swap™ interchangeable temperature control options.

FIG. 1 is a cut-a-way view of an AR 2000 rheometer. Rheometer 100 includes casting 110, optical encoder 120 (also known as a displacement transducer), motor and bearings assembly 130, measuring geometry 140, a temperature system (not shown) that is attached to rheometer 100 at mechanical magnetic coupling 150, and normal force transducer 160. The functionality of each of these components is generally known and is therefore not described herein.

The temperature system can be quickly attached to rheometer 100 at mechanical magnetic coupling 150. The information that identifies the temperature system to software of rheometer 100 is held in a programmable chip. The programmable chip is contained within the connector that plugs into socket 112 of casting 110. This connector also carries electrical signals and power to and from the temperature system.

A test sample is placed in measuring geometry 140. The test sample fills a gap between an upper measuring geometry and a lower measuring geometry. The lower geometry is not free to rotate and can, but not always, be part of the temperature control system. The upper member of measuring geometry 140 is connected to motor and bearings assembly 130. The lower member of measuring geometry 140 forms part of or is connected to the temperature system. When the test sample is placed within measuring geometry 140 and rheometer 100 is activated, the various properties of the test sample can be measured or otherwise calculated by rheometer 100. For example, when motor and bearings assembly 130 applies a force on the test sample, the temperature system obtains the temperature of the test sample, and other components of rheometer 100 can determine other raw parameters of the test sample. The raw data include, for example, torque, displacement, speed, temperature, phase, gap, and the like, are used together with the measuring geometry information to calculate rheological parameters such as shear rate, shear stress, modulus, compliance, etc.

Depending on the nature and characteristic of the test sample, measuring geometry 140 can be one of several types of geometries. For example, measuring geometry 140 can be one of cone-and-plate, plate-and-plate, concentric-cylinders, and torsion type geometries. Each type of measuring geometry is associated with a unique set of characteristics, information, or data. For example, a measuring geometry can be associated with, among other properties, a diameter, a cone angle, an inertia, and other information or data that is unique to the measuring geometry. In the case of cones type measuring geometry, each cone is associated with unique calibrated data.

Accordingly, it is important that correct information associated with the measuring geometry is used by the software or firmware of rheometer 100 to calculate rheological parameters of the test sample from the raw data. If the wrong measuring geometry file is selected in the software or the wrong dimensions are entered by a user, then when the sample measurement is carried out the results can be erroneous. Known problems or disadvantages associated with manual entry include operator error (in terms of geometry selection and parameter input) and the time required to select or setup a geometry. Thus, there is a need for a system and method that would eliminate or reduce operator errors at least in terms of geometry selection and parameter input, and to reduce the time required to select or setup a geometry. Circle 180 shown in FIG. 1 indicates the portion of rheometer 100 in which the present invention can be embodied.

SUMMARY OF THE INVENTION

The invention can be adapted for use with a number of different instruments that have detachable components. For example, any material testing instrument that has a performance envelope that can be modified by changing to a different type of measuring geometry can benefit from the invention. Specifically, instruments such as viscometers, texture analyzers, dynamic mechanical analyzers, rheometers, and the like, can incorporate the invention.

In one embodiment, the invention provides a detachable component of an instrument. The detachable component includes a connection portion that is configured to be attached to the instrument and a machine-readable device disposed on the detachable component. Information associated with the detachable component is retrievable by the instrument using the machine-readable device. The machine-readable device can be an optical device, a mechanical device, or a magnetic device. For example, the machine-readable device can be a bar code, a variable depth pattern, or a magnetic stripe. As stated above, the instrument can be a viscometer, a texture analyzer, a dynamic mechanical analyzer, and a rheometer. In the case of a rheometer, the detachable component may be, for example, the measuring geometry of the rheometer. The information retrievable using the machine-readable device can include, for example, one or more of serial number, type, material, dimensions, and calibration data of the detachable component. Preferably, the detachable component further includes means for holding a test sample.

In another embodiment, the invention provides an instrument that includes a connection configured to mate with a detachable component and a reader configured to read a machine-readable device disposed on the detachable component. Information associated with the detachable component is retrievable by the instrument using the machine-readable device. The information can include, for example, one or more of serial number, type, material, dimensions, and calibration data of the detachable component. Preferably, the instrument further includes an algorithm that receives the information from the reader. Preferably, the algorithm uses the information to perform an analysis on a test sample held by the detachable component.

In another embodiment, the invention provides a method that includes: (1) associating information related to a detachable component of an instrument on a machine-readable device disposed on the detachable component; (2) attaching the detachable component to the instrument; (3) reading the machine-readable device to retrieve the information associated with the detachable component; and (4) using the information to perform an analysis on a sample placed on the instrument.

In another embodiment, the invention provides an instrument that includes a detachable component, a reader, and an algorithm. The reader is configured to read a machine-readable device that is disposed on the detachable component. Using the machine-readable device, the instrument can retrieve information associated with the detachable component. The algorithm uses the information to analyze properties associated with a test sample held by the instrument.

The preferred embodiment of the invention is a rheometer. The rheometer of the invention includes a shaft, a measuring geometry, a reader, and an algorithm. The shaft is configured to be driven by a motor and bearing assembly. The measuring geometry is detachably attached to the shaft, and it has a machine-readable device disposed on it. The machine-readable device is associated with information related to the measuring geometry. The reader is configured to obtain the information associated with the measuring geometry based on the machine-readable device. The algorithm uses the information to analyze properties associated with a test sample.

BRIEF DESCRIPTION OF THE DRAWINGS

FIG. 8 is a flowchart showing exemplary steps associated with a preferred embodiment of the invention.

DETAILED DESCRIPTION OF THE INVENTION

Figure 1:
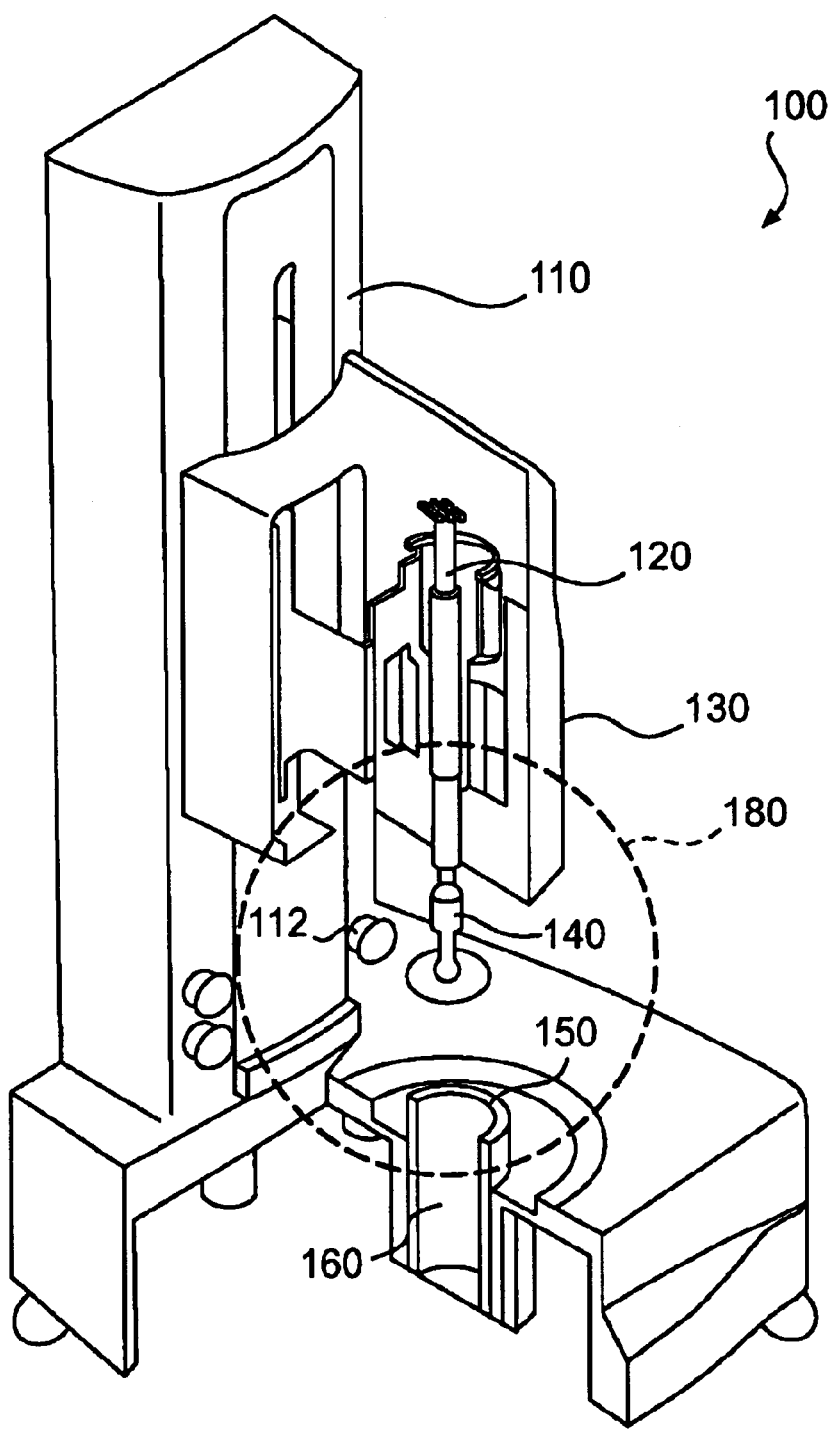
FIG. 1 is a cut-a-way view of a known rheometer.
Figure 2:
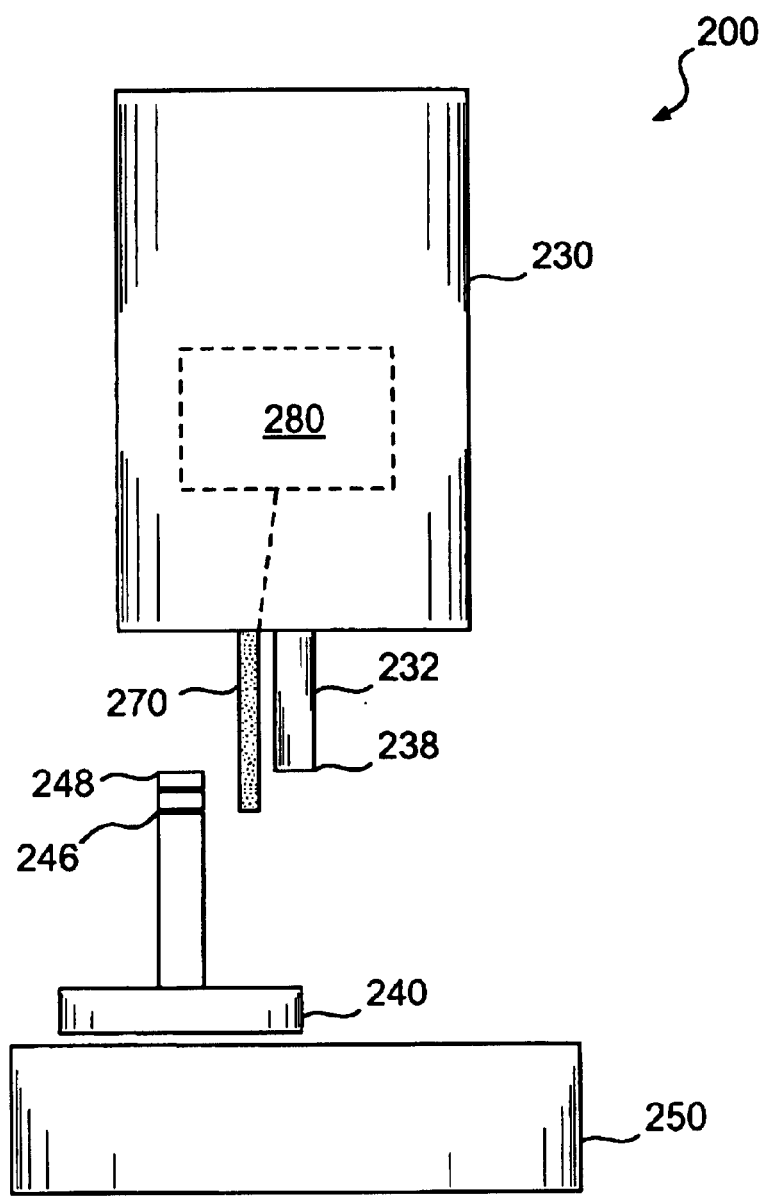
FIG. 2 is a schematic diagram showing a preferred embodiment of an enlarged portion of an instrument of the invention, before a detachable component is attached to the instrument.

FIG. 2 is a schematic diagram showing an enlarged portion of an instrument of the invention. In a preferred embodiment in which the instrument is a rheometer, the enlarged portion corresponds with the region indicated by circle 180 shown in FIG. 1. Instrument 200 can be any material testing instrument that has a performance envelope that can be modified by changing to a different type of detachable component. For example, instrument 200 can be a viscometer, a texture analyzer, a dynamic mechanical analyzer, a rheometer, or the like. To illustrate the preferred embodiment of the invention, instrument 200 is described herein as a rheometer and detachable component 240 is described herein as a measuring geometry of the rheometer. It is noted that detachable component 240 can be another component of the rheometer, including for example, a temperature system of the rheometer. Of course, detachable component 240 can be other components depending on what instrument 200 is.

Rheometer 200 includes motor and bearings assembly 230, measuring geometry 240, temperature system 250, and reader 270. These components are attached to a casting (e.g., casting 110 shown in FIG. 1). These components interact among themselves and with other components of rheometer 200, including an optical encoder (e.g., optical encoder 120) and a normal force transducer (e.g., normal force transducer 160) during material testing. One aspect of the present invention is embodied in detachable component 240. Another aspect of the invention is embodied in reader 270. Assembly 230 and temperature system 250 can be identical to assembly 130 and the temperature system discussed in the background section above, respectively.

Figure 3:
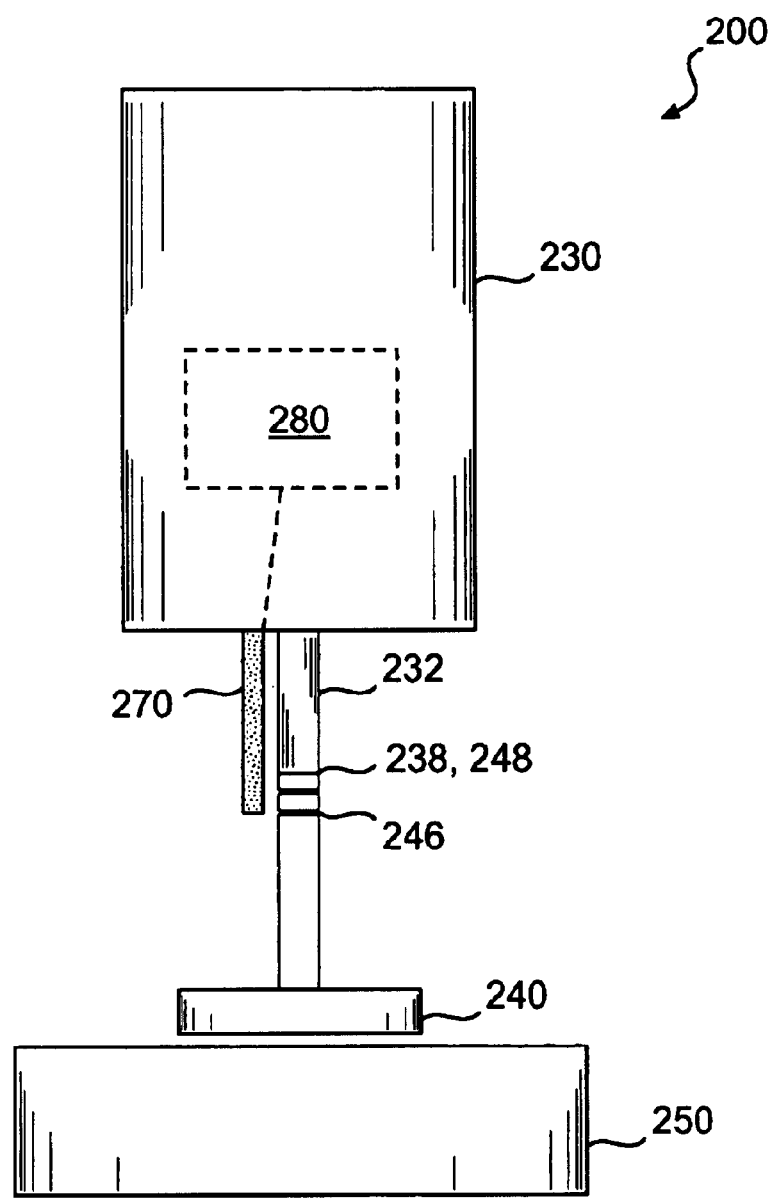
FIG. 3 is a schematic diagram showing the detachable component of FIG. 2 attached to the instrument.

Measuring geometry 240 is a detachable component of rheometer 200 and it can have several shapes. Exemplary shapes of measuring geometry 240 include those depicted in FIGS. 4, 5, 6, and 7. A test sample is placed in or otherwise held by measuring geometry 240. Measuring geometry 240 is then connected to rheometer 200. As depicted in FIGS. 2 and 3, upper end 248 of measuring geometry 240 is connected to lower end 238 of shaft 232, which is driven by assembly 230. The connection between lower end 238 and upper end 248 transfers a rotational movement of assembly 230 to the test sample.

In addition to upper end 248, measuring geometry 240 includes machine-readable device 246. Machine-readable device 246 can utilize one of several known technologies. Known technologies that can be used for machine-readable device 246 include optical, mechanical, magnetic, and other solutions. An exemplary optical solution incorporates the use of a bar code on machine-readable device 246. Alternatively, a mechanical solution can incorporate variable depth patterns (e.g., dimples) on machine-readable device 246. Preferably, machine-readable device 246 includes a magnetic stripe. The magnetic stripe can be similar to that disposed on commercial credit cards, but it is specifically configured to be robust enough for applications in rheometers. A known source of a magnetic ink that can be used to prepare the magnetic stripe is Ferron Magnetic Inks Ltd, 13 Grange Farm Road, Whitehall Road, Colchester CO2 8JW, The United Kingdom. Known coating techniques that can be used to apply the magnetic material on measuring geometry 240 are discussed in materials published on the Web site of Ferron Magnetics Inks Ltd.

Regardless of the types of technology used in machine-readable device 246, machine-readable device 246 is configured to be used to retrieve information associated with measuring geometry 240. The information can include, for example, one or more of type, material, dimensions, and calibration data of measuring geometry 240. The information can also be a serial number unique to measuring geometry 240.

Machine-readable device 246 can be located at any location on measuring geometry 240. Preferably, machine-readable device 246 is located near upper end 248. In this manner, machine-readable device 246 is more accessible to a reader, e.g., reader 270, which is described below.

Reader 270 is configured to read machine-readable device 246. For example, if machine-readable device 246 includes a bar code, reader 270 is a bar code scanner. In a preferred embodiment of the invention in which machine-readable device 246 includes a magnetic stripe, reader 270 is a magnetic reader.

The information obtained by reader 270 is transferred to algorithm 280. Algorithm 280 can be embodied in a firmware or a software. Algorithm 280 can be a member of rheometer 200 or it can be part of a machine external to and separate from rheometer 200.

Preferably, reader 270 is retractable. Preferably, reader 270 is extendable from assembly 230 to a lower position (see FIGS. 2 and 3) to read machine-readable device 246. Reader 270 is preferably retractable (partially or entirely) to a higher position into assembly 230 when not in use. A retractable reader serves several purposes including, for example, facilitating attachment of measuring geometry 240 to shaft 232 of assembly 230, reducing likelihood of damage to reader 270, and obviating interaction between machine readable device 246 and reader 270 during normal operation.

Depending on the type of technology employed in machine-readable device 246, reader 270 can be a sensor that is configured to obtained the information encoded on or otherwise disposed on machine-readable device 246. For example, reader 270 can be, but not limited to, a magnetic or an optical device. Machine-readable device 246 is preferably robust enough to maintain its readability after exposure to elevated temperatures, solvents, and other materials typically measured by rheometer 200.

One preferred embodiment of the invention enables automatically reading of the installed measuring geometry. As described above, measuring geometry 240 can be encoded with or otherwise configured to contain information concerning its serial number, type, material, dimensions, and calibration data. Through reader 270 and machine-readable device 246, algorithm 280 obtains the information when measuring geometry 240 is attached to rheometer 200. Machine-reader device 246 can be a bar code, a variable depth pattern, a magnetic stripe, or the like. Machine-readable device 246 is associated with information related to measuring geometry 240. If the information encoded into machine-readable device 246 is a unique serial number then this could be referenced to a database to retrieve the geometry information that can include, for example, one or more of type, material, dimensions, and calibration data of measuring geometry 240. The database is accessible to algorithm 280 via a host computer or a central server on the Internet.

Another advantage of knowing the current geometry of measuring geometry 240 is that the approximate position of the zero position can be known by rheometer 200. The zero position allows initiation of a zero gap routine without operator involvement. With the present invention, operator error in terms of geometry selection and parameter input is eliminated. Furthermore, the time required to select or setup a geometry is saved. Commercial applications of the invention includes a new feature on any material testing devices that allow interchangeable measuring systems.

FIGS. 4, 5, 6, and 7 are schematic diagrams of four different, exemplary measuring geometry 240.

Figure 4:
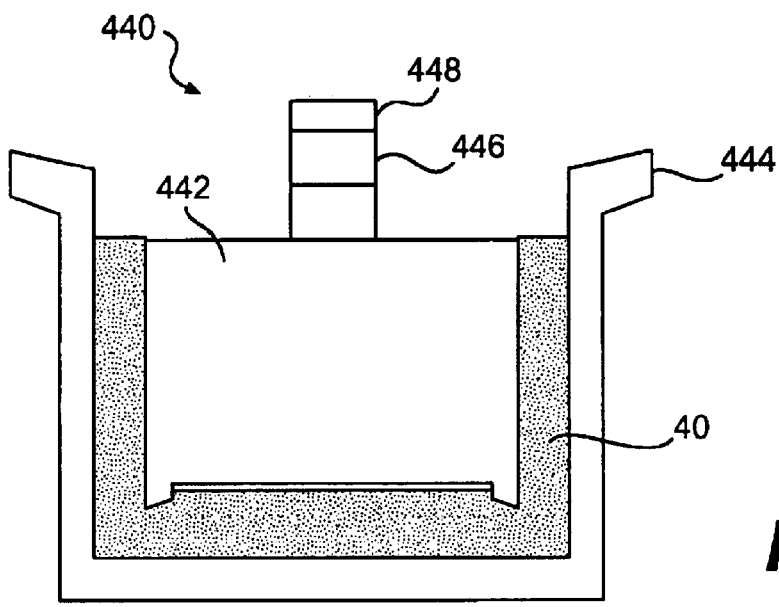
FIG. 4 is a schematic diagram showing a detachable component of the invention.

In FIG. 4, measuring geometry 440 holds sample 40 between inner cylinder 442 and outer cylinder 444. Upper end 448 is configured to mate with lower end 238. Machine-readable device 446 includes information associated with measuring geometry 440. The information includes, for example, unique serial number, cylinder type (e.g., conical, recessed, double gap), diameter, immersed height, material, gap temperature compensation value, and inertia. The information is either read directly or referenced to a database by way of the unique serial number.

Figure 5:
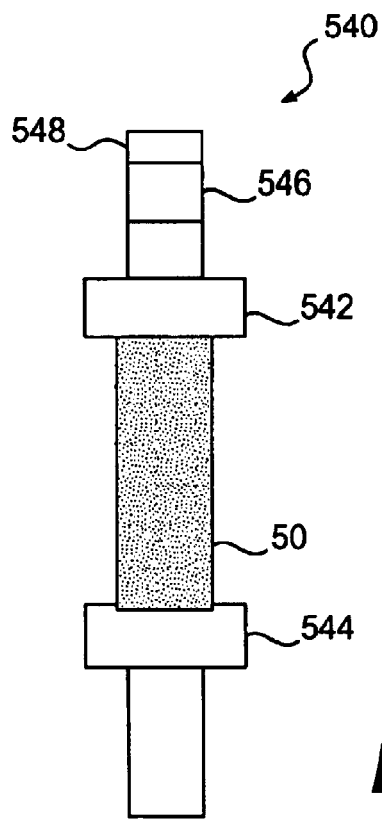
FIG. 5 is a schematic diagram showing another detachable component of the invention.

In FIG. 5, measuring geometry 540 holds sample 50 that is located between upper clamp 542 and lower clamp 544. Upper end 548 is configured to mate with lower end 238. Machine-readable device 546 includes information associated with measuring geometry 540. The information includes, for example, unique serial number and compliance. The information is either read directly or referenced to a database by way of the unique serial number.

Figure 6:
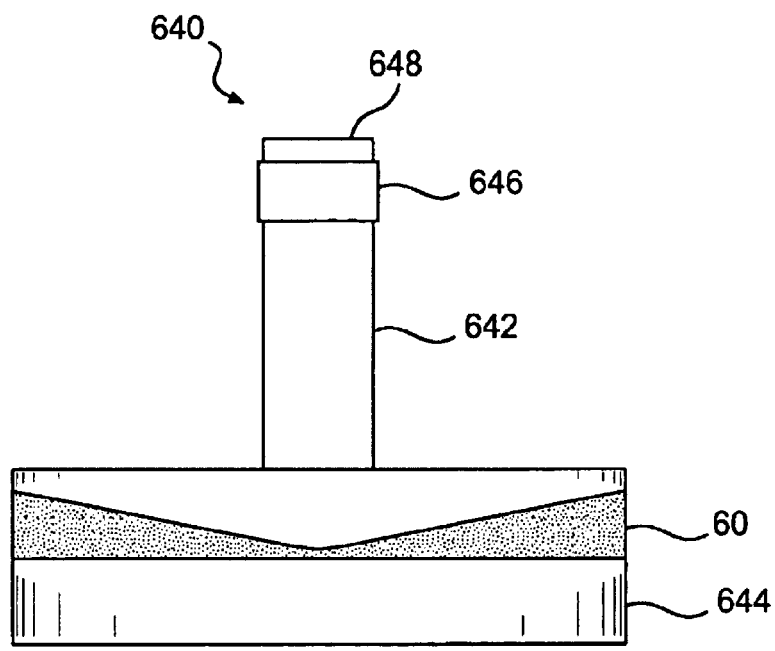
FIG. 6 is a schematic diagram showing another detachable component of the invention.

In FIG. 6, measuring geometry 640 holds sample 60 between cone 642 and plate 644. Upper end 648 is configured to mate with lower end 238. Machine-readable device 646 includes information associated with measuring geometry 640. The information includes, for example, unique serial number, diameter, cone angle, truncation, material type, inertia, and gap temperature compensation value. The information is either read directly or referenced to a database by way of the unique serial number.

Figure 7:
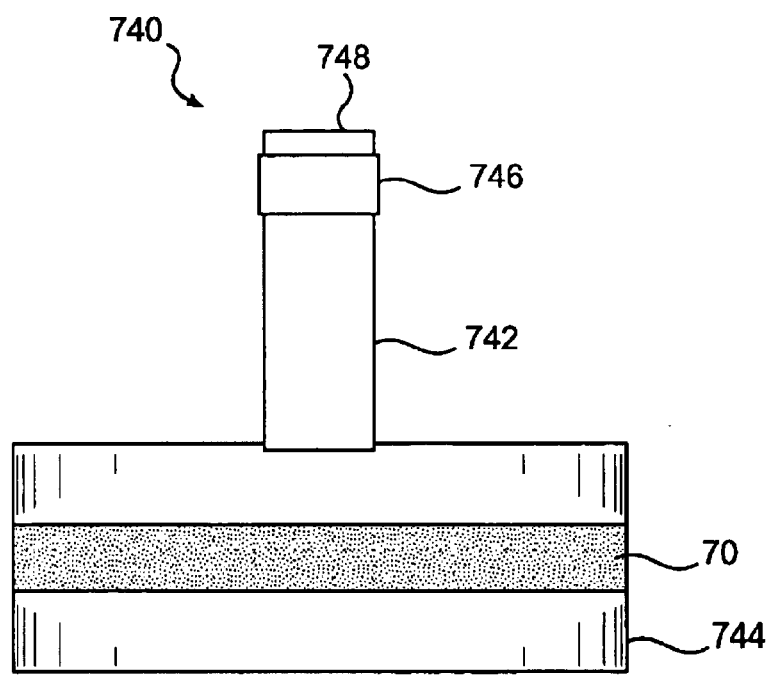
FIG. 7 is a schematic diagram showing another detachable component of the invention.

In FIG. 7, measuring geometry 740 holds sample 70 between upper plate 742 and lower plate 744. Upper end 748 is configured to mate with lower end 238. Machine-readable device 746 includes information associated with measuring geometry 740. The information includes, for example, unique serial number, diameter, material type, surface finish, compliance, inertia, and gap temperature compensation value. The information is either read directly or referenced to a database by way of the unique serial number.

The material type for each of measuring geometry 440, 540, 640, and 740 can be, for example, stainless steel, acrylic, aluminum, stainless steel with heat break, and titanium.

An alternative implementation of the invention is to provide a lookup table associating a unique serial number with information relating to each of measuring geometry 440, 540, 640, and 740. The unique serial number is read by the rheometer when the measuring geometry is attached to it. The information is then retrieved from the lookup table using the unique serial number.

Information associated with measuring geometry 440, 540, 640, and 740 is encoded on or otherwise contained within machine-readable devices 446, 546, 646, and 746, respectively. As described above, the information contained in machine-readable device 440, 540, 640, and 740 is readable by reader 270, and the information is then transferred to algorithm 280 for analysis of sample 40, 50, 60, and 70, respectively.

As indicated in FIGS. 4, 5, 6, and 7, a range of measuring geometries can used by rheometer 200. As shown in FIGS. 4, 5, 6, and 7, different types of measuring geometries have different characteristics, information, or data. For example, a measuring geometry can be associated with diameter, cone angle, inertia, and other information or data that is unique to the measuring geometry. In the case of cones type measuring geometry, e.g., measuring geometry 640, each cone is uniquely calibrated.

It is noted that reader 270 and machine-readable device 246 of rheometer 200 do not interfere with measurement operations of rheometer 200.

FIG. 8 is a flowchart showing exemplary steps associated with a preferred embodiment of the invention.

In step 802, information associated with a detachable component (e.g., measuring geometry 240) of an instrument (e.g., rheometer 200) is encoded on or otherwise contained within a machine-readable device (e.g., machine-readable device 246) that is disposed on the detachable component. It is noted that the encoding step is not necessarily performed on the instrument. For example, the geometries can be encoded as part of the manufacturing process, and the information can be read on the instrument.

In step 804, the detachable component is attached to the instrument. The attachment is made by mating an upper end of the detachable component (e.g., upper end 248) with a lower end of the instrument (e.g., lower end 238). Any known connection may be used.

In step 806, machine-readable device 246 is read by a reader (e.g., reader 270) of the instrument.

In step 808, the information is used to perform an analysis on a sample held by or otherwise placed on the instrument. For example, an algorithm embodied on the instrument (e.g., algorithm 280) can be used to perform the analysis.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. An instrument for testing a test sample, comprising:
   a performance envelope that is modifiable by changing detachable components associated with the instrument;
   a connection configured to mate with a detachable component; and
   a reader configured to read a machine-readable device disposed on the detachable component, wherein information associated with the detachable component is retrievable by the instrument using the machine-readable device, wherein the information includes mechanical properties of the detachable component, and
   wherein the instrument is configured to determine from the information an approximate position of the zero position and to initiate a zero gap routine without operator involvement.

2. The instrument of claim 1, wherein the reader is retractable.

3. The instrument of claim 1, further comprising an algorithm that receives the information from the reader.

4. The instrument of claim 1, wherein the instrument is a material testing instrument.

5. The instrument of claim 1, wherein the instrument is one of a viscometer, a texture analyzer, a dynamic mechanical analyzer, and a rheometer.

6. The instrument of claim 1, further comprising a computer containing a database that associates serial numbers with detachable component information, wherein a unique serial number is encoded in the machine-readable device, and wherein the information is retrievable from the database based on the unique serial number.

7. The instrument of claim 1, further comprising an algorithm that uses the information to perform an analysis.

8. The instrument of claim 7, wherein the analysis relates to material properties of a test sample held by the detachable component.

9. A method for testing a test sample comprising:
   associating information related to a detachable component of an instrument on a machine-readable device disposed on the detachable component, wherein the information includes mechanical properties of the detachable component;
   attaching the detachable component to the instrument;
   reading the machine-readable device;
   moving the detachable component with the instrument;
   using the information to perform an analysis on the test sample placed on the instrument,
   determining an approximate position of the zero position; and
   initiating a zero gap routine without operator involvement,
   wherein the instrument is a rheometer.

10. The method of claim 9, wherein the information includes one or more of serial number, type, material, dimensions, and calibration data of the detachable component.

11. The method of claim 9, wherein the machine-readable device is one of a bar code, a variable depth pattern, and a magnetic stripe.

12. The method of claim 9, wherein reading the machine-readable device comprises reading a unique serial number from the machine-readable device and retrieving the information from a table that associates the unique serial number with the information.

13. The method of claim 9, further comprising exposing the machine-readable device to the test sample.

14. An instrument for testing test samples, comprising:
   a performance envelope that is modifiable by changing detachable components associated with the instrument;
   one or more detachable components, each having a machine-readable device, wherein information associated with each detachable component is retrievable by the instrument using the machine-readable device, and wherein the information includes mechanical properties of the detachable component;
   a reader configured to obtain the information from the machine-readable device; and
   an algorithm that uses the information to analyze properties associated with a test sample in contact with the detachable component,
   wherein the instrument is a rheometer, and wherein the instrument determines from the information an approximate position of the zero position and initiates a zero gap routine without operator involvement.

15. The instrument of claim 14, wherein the information includes one or more of serial number, type, material, dimensions, and calibration data of the detachable component.

16. The instrument of claim 14, wherein the analysis relates to material properties of the test sample.

17. The instrument of claim 14, wherein the analysis relates to rheological properties of the test sample.

18. A rheometer comprising:
- a shaft configured to be driven by a motor and bearing assembly;
- a measuring geometry detachably attached to the shaft;
- a machine-readable device disposed on the measuring geometry, wherein the machine-readable device is associated with informing related to the measuring geometry, wherein the information includes mechanical properties of the measuring geometry;
- a reader configured to obtain the information from the machine-readable device; and
- an algorithm that uses the information to analyze rheological properties associated with the test sample,
- wherein the rheometer is configured to determine from the information an approximate position of the zero position and to initiate a zero gap routine without operator involvement.

19. The rheometer of claim 18, wherein the information includes one or more of serial number, type, material, dimensions, and calibration data of the measuring geometry.

20. The rheometer of claim 18, wherein the reader is retractable.

21. The rheometer of claim 18, wherein the machine-readable device is one of a bar code, a variable depth pattern, and a magnetic stripe.

* * * * *